United States Patent [19]

Luck et al.

[11] Patent Number: 4,488,911

[45] Date of Patent: Dec. 18, 1984

[54] NON-ANTIGENIC COLLAGEN AND ARTICLES OF MANUFACTURE

[76] Inventors: Edward E. Luck, 216 Robin Way, Menlo Park, Calif. 94025; John R. Daniels, 842 Las Casas, Pacific Palisades, Calif. 90272

[21] Appl. No.: 532,572

[22] Filed: Sep. 15, 1983

Related U.S. Application Data

[60] Continuation-in-part of Ser. No. 144,705, Apr. 28, 1980, now Defensive Publication No.

[51] Int. Cl.$^3$ .......................... C08L 89/06; C07G 7/00
[52] U.S. Cl. .................................... 106/161; 204/158; 210/637; 210/644; 210/645; 260/123.7; 264/202
[58] Field of Search ............................ 260/118, 123.7; 106/161, 155; 210/637, 644, 645; 204/158; 264/202

[56] References Cited

U.S. PATENT DOCUMENTS

| | | | |
|---|---|---|---|
| 2,919,999 | 1/1960 | Reissman et al. | 106/161 |
| 2,920,000 | 1/1960 | Hochstadt et al. | 106/161 |
| 3,131,130 | 4/1964 | Oneson et al. | 106/161 |
| 3,303,038 | 2/1967 | Klevens | 106/155 |
| 3,314,861 | 4/1967 | Fujii | 260/117 |
| 3,503,877 | 3/1970 | Berry | 210/644 |
| 3,949,073 | 4/1976 | Daniels et al. | 424/177 |
| 4,089,333 | 5/1978 | Utsuo et al. | 128/156 |
| 4,140,537 | 2/1979 | Luck et al. | 106/161 |
| 4,233,360 | 11/1980 | Luck et al. | 106/155 |

FOREIGN PATENT DOCUMENTS 903975  4/1960  United Kingdom .

*Primary Examiner*—Theodore Morris

[57] ABSTRACT

Collagen, available from domestic animals, is freed of noncollagen proteins, glycosaminoglycans and lipids by enzymatic treatment with a proteolytic enzyme to yield a product which is soluble in dilute acidic aqueous solutions (collagen in solution—CIS). The naturally occurring collagen is modified by removal of certain terminal peptide chains, which are described as telopeptides. The modified collagen, so derived, is described as atelopeptide collagen. Native collagen is immunogenic, while atelopeptide collagen is nonimmunogenic or possessed of a negligibly low level of immunogenicity.

The collagen in solution is then treated according to a specific regimen under conditions whereby the collagen slowly separates from solution while exposed to mild shear forces. This procedure results in the formation of a fibrous precipitate composed of regularly ordered fibers of collagen possessed of a rope-like structure. These resulting aggregates are referred to as native fibrous micropolymers (NFM). Once the regimen or procedure is completed, and the fiber mass has been formed, the fibrous micropolymers may be freed of salt, taken up in a different solution or modified. For example, cross-links may then be introduced to stabilize the fibers. The products find wide use as packing, membranes, fibers, bags, supports, integuments, and are especially suitable for biologic implantation or application.

14 Claims, No Drawings

NON-ANTIGENIC COLLAGEN AND ARTICLES OF MANUFACTURE

CROSS-REFERENCE TO RELATED APPLICATIONS

This application is a continuation-in-part of application Ser. No. 144,705 filed Apr. 28, 1980, which was a divisional of application Ser. No. 945,723, filed Sept. 24, 1978, now U.S. Pat. No. 4,233,360 issued Nov. 11, 1980 which was a divisional of application Ser. No. 744,536, filed Nov. 24, 1976, now U.S. Pat. No. 4,140,537 issued Feb. 20, 1979 which was a continuation-in-part of application Ser. No. 624,678, filed Oct. 22, 1975, now abandoned.

BACKGROUND OF THE INVENTION

1. Field of the Invention

Collagen is the principal structural protein present in vertebrates. It has many properties which make it particularly desirable for the fabrication of medically useful devices. Natural collagen is readily available from a variety of domestic animals. The major portion of its structure varies little between mammalian species; and the positions of the distinguishing and structurally significant amino acid residues (glycine, proline, and hydroxyproline) are uniquely consistent in the main helical portion of the atelopeptide collagen. This fundamental similarity is associated with characteristically low levels of immunogenic activity. Many immunogenic determinants are in the nonhelical protein appendages extending from the terminal portions of the native molecule. These nonhelical extensions, telopeptides, represent less than five percent of the naturally occurring molecule and can be removed through limited proteolysis. The treatment produces a disaggregation of discrete undenatured collagen molecules from the fibrous matrix (i.e. solubilization) and a substantial reduction in the ability of such molecules to elicit an immunologic response in a host different from the collagen source.

While the telopeptides are important sites of immunogenicity and their presence in collagen is undesirable in medical applications, the telopeptides play an important structural role in naturally occurring collagen. The telopeptides are the primary sites of both intra- and intermolecular cross-links. It is this portion of the molecule which provides the structural integrity of native collagen fibers. Moreover, there is evidence that the telopeptides direct the process of fibrogenesis through promoting the orderly accretion of constituent molecules into large structurally signficant fibers. Thus, the removal of the telopeptides also removes that portion of the molecule which in the natural state appears essential to the formation and subsequent stability of native collagen fibers.

2. Description of the Prior Art

Two survey articles concerning collagen are by Bornstein; "The Biosynthesis of Collagen", *Annual Review of Biochemistry* (1974) 43:567, and by Stenzel, et al, "Collagen As a Biomaterial", *Annual Review of Biophysics and Engineering* (1974) 3:231. Patents concerned with forming atelopeptide collagen are U.S. Pat. Nos. 3,034,852; 3,121,049; 3,131,130; 3,314,861; 3,530,037; and 3,949,073.

Patents concerned with various articles of manufacture prepared from collagen include U.S. Pat. Nos. 2,920,000; 2,934,446–7; 3,014,024; 3,491,760; 3,562,820; and 3,563,228.

Other articles will be referred to in the text, when appropriate, in relation to specific aspects of the subject invention.

SUMMARY OF THE INVENTION

The subject invention is concerned with the formation of fibers of collagen substantially free of the immunogenic nonhelical terminal portion, i.e. telopeptides. The fibrous products formed in the subject invention are of relatively large diameter which appear in scanning electron micrographs as twisted interwined fibers with a rope-like structure. The collagen fibers of this invention have substantially the same structure as natural collagen and may be used as formed, or cross-linked, to provide a variety of medically useful products: sponges, prosthetic devices, films, membranes, sutures, etc.

Native collagen is liberated from noncollagen connective tissue constituents (lipids, sugars, proteins, etc.) and isolated after subjecting it to proteolytic enzymatic treatment by an enzyme other than collagenase. The enzymatic treatment is maintained for a time sufficient to achieve a substantial removal of the telopeptides and to provide a collagen material which is soluble in aqueous media of reduced pH.

The resulting collagen in solution is then treated in accordance with a regimen in which the acidic medium is modified to provide for a slow precipitation of the atelopeptide collagen while the fluid medium is simultaneously exposed to sustained shear. The collagen separates from solution as fibrous microaggregates ("native fibrous micropolymers") which may be freed of the salt solution or taken up in a different solution. The fibrous aggregates may be used directly for a variety of purposes or may be cross-linked to provide fibers having substantial structural integrity and macroscopic dimensions. Depending upon the intended use of the native fibrous micropolymers, the fibers may be treated in a variety of ways to prepare various articles of manufacture.

DESCRIPTION OF THE SPECIFIC EMBODIMENTS

A method is provided for preparing articles derived from nonhuman collagen which have low immunogenicity or are nonimmunogenic. Collagen may be obtained in commercially useful amounts from the connective tissues of a wide variety of domestic animals such as cattle, swine, etc. The native collagen is most conveniently obtained from tendons or skin and is freed from extraneous matter such as lipids, saccharides and noncollagen protein, so as to leave the collagen protein free or substantially free of other connective tissue materials. Native collagen fibers are composed of regularly arranged subunit structures referred to as collagen molecules. Each collagen molecule is about 3000Å long and 15Å in diameter. This long, rigid rod-like structure consists of three polypeptide chains wounds together in a triple helical configuration. Typically two of the constituent chains are identical in composition and the third is different. A characteristic distribution of amino acid residues along the length of any given polypeptide strand, wherein repeating triplets contain glycine at every third position, favors the formation of a helical configuration. The individual collagen units form fibrils which associate to form fibers.

The nonhelical terminal portions of the native collagen molecule, the telopeptides, extend as random coils from the amino and carboxy ends of the molecule.

The telopeptides appear to serve a number of functions in the formation of the native collagen fiber. The telopeptides serve as the primary sites for cross-linking intramolecularly (between constituent polypeptide chains in the native collagen molecule) and intermolecularly (between two or more native collagen molecules). In addition, the telopeptides facilitate the arrangement of the individual collagen molecules in a pattern which provides for the regular structure of native fibrous collagen. The telopeptide portions of native collagen are believed to be the major sites of its immunogenicity. Therefore, in order to minimizes the immunogenicity of the collagen to be used for the purposes indicated previously and subsequently elaborated upon, it is desirable that the telopeptides be removed.

In accordance with this invention, atelopeptide collagen is produced free of noncollagen protein and other substances present in naturally occurring connective tissues. This collagen is soluble in dilute aqueous acid, e.g. 0.1M acetic acid. Any insoluble collagen, if present, may be removed by filtration, centrifugation, or other means.

Once the collagen solution is obtained it may be employed for preparing native fibrous micropolymers (NFM), that is, collagen fibers prepared from atelopeptide collagen. The procedure for preparing the NFMs involves a slow precipitation of the collagen from the solution while subjecting the aqueous medium to mild shear. The conditions under which the precipitation of the collagen is achieved can be varied widely with some conditions being preferred over others. The temperatures employed generally range from 4° to 40° C., more usually from 15° to 37° C. and preferably from 15° to 25° C. The pH is generally in the range of about 6 to 10.5, usually in the range of about 7 to 9.5 preferably in the range of about 7 to 9. A wide variety of salts may be used, usually alkali metal salts, both neutral and alkaline, which alkali metals of atomic number 3 to 19, more particularly sodium and potassium, with mono- and polyvalent cations, particularly halides e.g. chloride, and phosphate (including mon- and di-acid phosphate). The concentration of the salt may vary widely with the other conditions employed, e.g. temperature and protein concentration, as well as with the particular salt. Applicable concentrations generally range from about 1 mM to 200 mM, more usually 20 mM to 150 mM, with salts of polyvalent anions generally ranging from 5 mM to 75 mM and salts of monovalent anions ranging from about 100 mM to 200 mM. The concentration of collagen may vary from relatively dilute to relatively concentrated solutions, generally ranging from about 0.1 mg/ml to 20 mg/ml, more usually from about 1 mg/ml to 15 mg/ml. Times in which the precipitation will occur vary from about 1 hour to 24 hours, usually about 2 hours to 12 hours, and preferably about 4 hours to 8 hours.

Various techniques may be used to obtain the desired rate of precipitation of collagen while applying the mild shearing. One technique is heat gelation, wherein a constant or slowly increasing temperature is employed to bring about precipitation of collagen in the presence of salt. Generally, the temperature range is from about 0° to 40° C., the temperature being slowly raised from about 0° C. to 10° C. to a temperature of about 30° to 40° C. Salt concentrations generally vary from about 75 mM to 200 mM. Alkali metal halides, e.g. sodium chloride, are preferably employed. The pH is usually from 6.5 to 8.5, preferably 7 to 8. Particularly preferred conditions are physiological conditions, namely 130 mM NaCl pH 7.4, with a final temperature of about 37° C.

Another technique is to provide for a slow increase in ionic strength and, optionally, temperature with the collagen in solution. This can be achieved by employing dialysis with a polyvalent salt dialysate, and thereby slowly raising the salt concentration (or ionic strength) in the aqueous collagen solution. One can adjust the pH of the medium initially or incrementally, typically by employing an alkaline salt in the dialysate. Usually, the dialysate has a salt concentration of about 5 mM to 100 mM, more usually 10 to 50 mM, particularly of disodium phosphate. The final pH of the medium is generally 6.5 to 10.5, more usually 7 to 9.5 and preferably 7 to 8.5.

Another procedure is that of continuous dialysis at ambient or moderately reduced temperatures while changing the dialysate from a dilute mildly acidic solution (generally a dilute carboxylic acid solution), to a mildly basic salt solution, while slowly increasing the ionic strength or salt concentration by using a dialysate of increasing salt concentration. With increasing ionic strength or salt concentration, the temperature may also be increased, until a nascent fiber mass is obtained. The nascent fiber mass is freed of any nonfibrous material, and may be treated in a variety of ways depending on the intended use.

Fibrous material may be tanned and used in a wide variety of medical applications as gels, films, sponges, bags, tubes, laminates, threads, fibers and specialized three-dimensional structures for unique physical and biological applications. Nontanned or noncrosslinked fibrous collagen may be used as implants, e.g. packing, in combination with collagen in solution as emulsions, prosthetic devices, and the like.

In describing the subject invention, three steps will be considered. The first step is the purification of native collagen and its transformation into collagen in solution (CIS). The second step is the transformation of the CIS into native fibrous micropolymers (NFM) and optionally cross-linking or tanning the micropolymers. The third step is the use of the micropolymers either with or without cross-linking, for the fabrication of various articles or the formation of compositions.

COLLAGEN IN SOLUTION

Collagen can be obtained from a wide variety of domestic animals and may be derived from the skin, tendon, or any other naturally occurring structural element having high collagen content. The intitial stage is to clean the skin or tendon physically so as to remove some noncollagen materials such as hair, fat, carbohydrates, mucopolysaccharides and the like. See for example U.S. Pat. Nos. 2,934,446 and 3,121,049 and Chvapil et al, *Medical and Surgical Applications of Collagen,* "Connective Tissue Research" (1973) 4.

To enhance the ease of purification and facilitate the enzymatic removal of the telopeptides the collagenous material is subjected to various mechanical treatments, such as dissection, grinding, high speed shearing, milling and the like. Depending upon the particular treatment, the collagen may be wet or dry, frozen or cooled, with grinding and high speed shearing preferably being wet processes, and milling being a dry process.

Coarsely divided connective tissues are swollen in aqueous acidic solutions under nondenaturing conditions. Further dispersion is achieved through extensive wet grinding to facilitate enzyme access to the native collagen. Preferably dilute acid solutions at low temperatures are employed to minimize denaturation. Suitable acids are acetic, malonic, or lactic acids, or other lyotropic carboxylic acids having pK values from about 2 to 5 at 25° C. Concentrations of acid in the dispersion medium range from about 0.01 M to 1.0 M and temperatures may vary from 4° C. to about 25° C.

In the subject invention, a preferred embodiment is to employ as a source of collagen tendon or skin from relatively young domestic animals, e.g. calves, whereby the collagen-containing material is separated from adjacent tissued by dissection, soaked in dilute acid at 20° C. and ground while wet. This technique is found to provide a homogeneous dispersion of connective tissue which is readily attacked by subsequent chemical and enzymatic treatment, so as to provide an efficient means for achieving collagen in solution.

The dispersion which is obtained by treatment with acid is a viscous dispersion containing native collagen microaggregates and a small amount of native collagen in solution.

The viscous product, which may now be referred to as dispersed swollen collagen, is subjected to enzymatic treatment to remove the telopeptides and to produce soluble atelopeptide collagen. Various proteolytic enzymes may be employed which preferentially attack the telopeptides, while leaving the major portion of the molecule intact. Illustrative enzymes include pepsin, trypsin, pronase, etc. See U.S. Pat. Nos. 3,131,130 and 3,530,037.

Depending upon the particular enzyme employed, the conditions for the enzymatic cleavage of the telopeptides will vary. With pepsin an acidic solution is employed, generally at a pH of about 2 to 4. The concentration of the enzyme varies from about 0.001 to 10 weight percent based on the weight of the collagen present. The collagen concentration generally varies from 0.5 g/l to 10 g/l, more usually from about 1 g/l to 5 g/l.

Preferably, the acidity is provided by a carboxylic acid in a concentration of about 0.01 M to 1 M. If necessary, the pH can be adjusted by the addition of a mineral acid, e.g., hydrochloric acid.

The temperature at which the enzymatic treatment is carried out generally ranges from about 0° to 30° C., more usually from about 10° to 20° C. The time for the treatment varies from about two days to not more than about two weeks. The progress is monitored periodically until substantially complete solubilization is achieved. The solution reaches a relatively constant viscosity.

The resulting solution is now treated to separate the soluble atelopeptide collagen from insoluble collagen, enzyme, and the amino acids and telopeptide units which are the product of the proteolytic treatment, as well as any other noncollagen material which has been released as a result of the enzymatic degradation.

Primarily, the treatment involves separations, precipitations and dialysis against various solutions of different ionic strength. Moderate temperatures are employed normally from 4° to 30° C. and salt solutions of varying ionic strength or concentration, generally from about 0.1 M to 3.5 M, depending upon the particular salt. Ionic strengths are usually of about 0.01 to 3.5.

Conveniently, the solution is treated with an alkaline material, e.g. sodium hydroxide, to raise the pH to at least about seven, to inactivate the enzyme. Alternatively, neutral salt solutions, e.g. NaCl, of about 0.5 to 5 weight percent may be employed as a dialysate in a free flow dialysis at a pH of at least seven and not greater than about ten. After inactivating the enzyme, nonsolubilized contaminants which have been precipitated during the inactivation treatment are filtered off to yield a filtrate which contains collagen in solution.

The collagen in solution is precipitated as part of a purification treatment, for example, by adding a neutral salt to the solution to a concentration of about 10 to 30, usually 20 percent (weight/volume: g/l). Various alkali metal halides, e.g. NaCl, may be used. The resulting precipitate is isolated, for example by centrifugation. Further treatment includes exchanging with a dilute carboxylic acid, e.g. acetic acid (0.05 M to 0.5 M), in the presence of aqueous NaCl (0.001 to 0.1 weight percent) with precipitation by addition of NaCl (3 to 20 percent weight/volume) and resolubilization to insure the purity of the atelopeptide collagen.

Specifically, the procedure may involve an initial precipitation by use of a neutral salt (at least 15 to 20 weight percent), isolation of the precipitate, redissolving in dilute acid, e.g. a carboxylic acid at about 0.05 M to 1 M, filtration, reprecipitation of the collagen with about 2 to 10 weight percent aqueous salt solution, isolation, redissolution with a dilute carboxylic acid, with repetition of the purification process until the atelopeptide collagen has been obtained in the desired degree of purity. The atelopepitde collagen is then resuspended in dilute acid solution, generally a carboxylic acid, at a concentration of acid of about 0.01 M to 0.5 M.

Precipitation of the collagen can be achieved in a variety of ways, such as the addition of neutral salt, decrease in pH in the presence of a neutral salt, etc. Preferably, mild conditions are employed to prevent denaturation and disruption of the natural rod-like character of collagen.

The atelopeptide collagen may now be concentrated, for example by resistence dialysis to a concentration of about 1 mg/ml to 20 mg/ml. The viscosity of this collagen in solution will typically be in the range of about 1500 to about 5000 cp. The clear solution of atelopeptide collagen in relatively free of higher aggregates. The purified atelopeptide collagen is now ready to be used for the formation of native fibrous micropolymers.

NATIVE FIBROUS MICROPOLYMERS

The collagen in solution is now treated to form the NFMs. A number of methods have been previously described. The preferred method is first to dialyse the collagen in solution with a dilute carboxylic acid solution and then dialyse the resulting acidic solution against a dilute aqueous solution of an inorganic alkaline polyvalent-anion salt, while raising the pH in the dialysis medium to neutral (7.0) or somewhat greater, generally less than 8.5. The dialysis bag is rotated to impart moderate shear to the collagen medium. During the dialysis, the salt concentration slowly increases in the dialysis bag to a level appropriate for the formation of NFMs.

The shear stress applied to the solution in a rotating container depends on what proportion of the solution rotates with the container to what proportion is stationary. Assuming a forced vortex solution (uniform velocity gradient) shear stress is independent of the container radius and is everywhere constant (except at the center). In this case shear stress is approximated by the formula $\tau = \mu\omega$ where $\mu$ is the viscosity of the solution in poises, $\omega$ is the rotational velocity in radians/sec and $\tau$ is the shear stress in dynes/cm$^2$. Velocity will usually be in the range of about 2 to 100 rad/sec, more usually about 5 to 50 rad/sec. Accordingly, the shear stress applied to the solution will usually be about 30 to about 5000 dynes/cm$^2$, more usually about 75 to 2500 dynes/cm$^2$.

In one simplified technique the collagen in solution is dialysed against a dilute carboxylic acid solution (see below) at ambient temperature, then dialysed with rotational shear against dilute alkaline phosphate e.g. 0.02 M disodium phosphate for a sufficient period of time, until micropolymers form. Usually two to eight hours (preferably about four to six hours) at ambient temperatures are required, although temperatures of about 15° C. to 40° C. can be used. The NFMs which form are collected by centrifugation, washed with water and stored. The ranges set forth previously are applicable to this procedure.

Alternatively, the collagen in solution is introduced into an apparatus having semi-permeable walls and capable of moderate rotation, generally at about 20 to 1000 rpm. Rotation at about 50 to 500 rpm is preferred. The diameter of the collagen solution-containing cell, e.g. a dialysis bag, is generally about 1 to 5 cm, more usually 2 to 3 cm. Initially, the collagen solution is dialyzed against a dilute carboxylic acid solution at moderate temperatures (0° to 10° C.), with the carboxylic acid concentration being about 0.001 M to 0.1 M, preferably about 0.001 M to 0.1 M. The time period between changes of the dialysate is not critical and may be varied widely, each dialysis being for about one to twelve hours, more usually from about two to eight hours, and conveniently over periods of from four to six hours.

After dialysis with the carboxylic acid, dialysis is then begun with an alkaline salt solution, preferably an alkali metal phosphate solution e.g., disodium phosphate. Initially, the salt solution is at a low concentration, generally from about 0.01 M to 0.05 M and at a temperature below about 10° C. The concentration of the salt in the outer fluid and the temperature are slowly raised so that in a period from about 10 to 36 hours, the concentration of the salt will level off at about 0.1 M to 0.5 M, preferably at about 10° to 20° C., preferably to about 12° to 16° C. By increasing the concentration of the salt in the outer fluid, the ionic strength is also raised. The outer fluid is next exchanged for distilled water, and ultimately for saturated NaCl. The temperature is maintained between 20° and 40° C. and the pH is held below 8, preferably between 5 and 8, and ideally at about 7.4.

During this period of time, fibroneogenesis occurs so that precipitation and aggregation of embryonic fiber masses is noticed. Once the nascent fiber mass has appeared and the terminal temperature and salt concentration have been achieved, the fibrils are freed of the disodium phosphate salt. One method is by dialysis, first against dilute salt, e.g. disodium phosphate at a concentration in the range of about 0.01 M to 0.05 M, followed by dialysis against distilled water. Alternatively, the fibrils may be dialyzed against saturated aqeuous NaCl. Ambient temperatures are satisfactory (approximately 20° to 25° C.).

The collagen products obtained by the above described techniques are found by scanning electron microscopy of a statistically significant number of samples to be colinearly arrayed aggregates of fibers having for the most part mean diameters in excess of 500 nm, usually of 1000 nm or greater. The fibrils forming the fibers appear intertwined or twisted as visualized by scanning electron microscopy. This is to be contrasted with prior art reconstitution techniques, such as thermal gelation of collagen in solution, which leads to randomly dispersed monofilaments having mean diameters of about 140 nm and a range of diameters extending from about 50 to 280 nm.

The resulting fibers may now be tanned to form a stable covalently linked collagenous material. Various tanning means may be employed which are well known in the art. These tanning techniques include treatment with monoaldehydes, e.g. formaldehyde and acetaldehyde; dialdehydes, such as succinaldehyde and glutaraldehyde; chrome tanning agents; and the like. Besides chemical tanning agents, the collagen molecules may be linked by exposure to ultraviolet or gamma radiation in an inert oxygen-free atmosphere. (During the tanning and subsequent dialysis, a flocculent precipitate may form and, prior to the washing of the fibers, the fibers may be separated mechanically from the flocculent precipitate.)

After tanning the resulting aggregates may be collected, rinsed, dialyzed against a dilute carboxylic acid, concentrated, and held in a swollen mass or lyophilized for future use.

ARTICLES OF MATTER

The noncross-linked or cross-linked atelopeptide collagen may be used directly as a gel. As a gel, the atelopeptide collagen can be used as a vitreous body. See Dunn et al, *Trans Amer Soc Artif Int Organs* (1971) 17:521 and Dunn et al, *Surgical Forum-Ophthalmic Surgery* (1974) 492. The gel can also be used as a wound covering. The collagen can be dried and formed as a flour or mat. Hart, *Amer J of Surgery* (1970) 120:330.

For an extensive discussion of collagen as a biomedical material, see Chvapil, et al, "Medical and Surgical Applications of Collagen", *Connective Tissue Research* (1973) 4.

The collagen can be readily employed in the formation of membranes by simply coating an inert surface with the cross-linked or noncross-linked collagen dispersed in an aqueous medium and allowing the solvent to evaporate. Various mechanical properties can be imparted to the membrane by the degree to which the atelopeptide collagen has been cross-linked. Colagen membranes can also be prepared by extrusion, so that flat sheets, circular casings or other structures can be prepared. The membranes can be so cross-linked as to have sufficient strength to retain their own integrity, or they can be used with supports. Films can be made having thicknesses of about 0.1 to 50 mils. Thicker films may be a single film or a plurality of films which have been adhered together.

Preparation of collagen dialysis membranes and their properties may be found in Nishihara et al, *Trans Amer Artif Int Organs* (1967) 13:243; Rubin, A. et al, ibid (1968) 14:169; Stenzel et al, ibid (1969) 15:114; and Stenzel et al, ibid (1971) 17:293.

The formation of films into articles is described in U.S. Pat. Nos. 2,920,000 and 3,562,820.

Fibers can be prepared which find uses as sutures, thread, woven articles and the like. See Stenzel et al, "Collagen as a Biomaterial", supra and Chvapil et al, supra.

The collagen can be further used for the formation of sponges. Sponges can be prepared having varying degrees of cross-linking or porosity, by freezing a degassed aqueous suspension of fibers and subliming the water or by employing blowing agents or other known techniques. Thus, a sponge can be prepared having varying degrees of permeability or porosity along a cross section. See Chvapil et al, supra.

Laminates can be prepared by freezing fibers to sponges, sponges to sponges, and the like, to form multilayered articles with unique properties.

A burn dressing can be prepared from foamed cross-linked NFMs and a film prepared from a dispersion of cross-linked and noncross-linked NFMs. In preparing the burn dressing, a foam is prepared by dispersing NFMs in an aqueous medium at a relatively high concentration, about 50 to 100 mg/ml, and lyophilizing the mixture to form a foam. The foam structure is stabilized by cross-linking, e.g. by treatment with formaldehyde vapor or solution.

A thin collagen film is then laminated to one side of the foam. The film is composed of a minor proportion by weight, 10 to 40 percent, of noncross-linked collagen and the remainder cross-linked collagen. The film can be bonded to the foam by spraying a concentrated dispersion on the foam, or by freezing the NFM slurry, applying the foam to the frozen slurry and then slowly drying at ambient pressures and mildly elevated temperature, less than about 40° C.

The collagen of this invention can be used as a vehicle for drug delivery, by incorporating a drug into a collagen film or particle. Bags can be employed for implantation, with the bags containing drugs or physiological fluids.

In addition, emulsions can be prepared of collagen in solution and fibrous micropolymers wherein the latter may not be cross-linked. These compositions can be used directly as implants or coatings or for the fabrication of articles, such as those described above. Normally, the collagen in solution will be from about 0.01 to 10 weight percent collagen and the fibers will be from about 0.1 to 10 weight percent.

The atelopeptide collagen which has been highly cross-linked can be used in the formation of various prosthetic devices for replacement of defective bond structures.

The various forms of the atelopeptide colagen have a wide variety of applications in the treatment of burns, replacement of vitreous, replacement of blood vessels (tubes), as burn dressings or coverings for wounds, treatment of bone defects, as drug-delivery systems and the like. The collagen may be a single film or a plurality of films or laminates; it may be used by itself or in combination with supports, or fibers or filaments, or the like.

In preparing the articles, the fibrous micropolymers may be used by themselves or in combination with collagen in solution and the system cross-linked, whereby intermediate highly oriented fibers act as a matrix onto which coalesce the partially oriented or randomly oriented filaments derived from atelopeptide collagen.

EXPERIMENTAL (All temperatures not otherwise indicated are in degrees Centigrade. All pressures not otherwise indicated are in millimeters Mercury. All percentages not otherwise indicated are weight percent.)

Bovine achilles tendon and fresh hides from one-month old calves, obtained fresh from slaughter, are separated from adjacent tissues by dissection, and suspended in acetic acid solution, 0.5 M, pH 3.0, 22° and mechanically dispersed by repeated passes through a Toledo meat chopper at 15°. The collagen is now a swollen dispersion of native collagen microaggregates admixed with a small amount of native collagen in solution.

To the acidic fluid is added pepsin (2×crystallized) to provide a concentration of 10 weight percent based on collagen and the mixture is maintained at 20° for four days. After neutralizing the solution by the dropwise addition of dilute sodium hydroxide, the mixture is allowed to stand for two hours at 4°.

The resulting opalescent mixture is filtered through a cake of diatomaceous earth.

To the filtrate is added sodium chloride to provide a concentration of 200 g/l and the resulting precipitate collected by centrifugation at 15,000 g for 30 minutes. The precipitate is dissolved in 0.1 M acetic acid to the original volume, the solution filtered through a diatomaceous cake and sodium chloride added to the filtrate to a final concentration of 50 g/l. After two hours at 4°, the mixture is centrifuged at 15,000 g for 30 minutes and the precipitate separated from the supernatant fluid and dissolved in 0.1 M aqueous acetic acid. This is now a highly purified and telopeptide-poor solution of collagen. Its viscosity is about 3000 cp.

The above solution is introduced into a dialysis tube of one inch diameter. The tubing is closed at each end leaving at one end a long segment which is wrapped around a two-inch long teflon-coated bar magnet and fastened by means of a rubberband. A small amount of air is trapped in the dialysis bag, which aids in its remaining vertical in the surrounding dialysis fluid. A four liter beaker is filled with 1 mM acetic acid, cooled to 4° and the beaker placed atop a magnetic stirring device with the dialysis bag immersed in the aqueous acetic acid solution.

The dialysis bag is rotated at about 200 rpm (approx 20 rad/sec), while the entire system is maintained in a cold room at 4°. The outer fluid is exchanged for fresh 1 mM aqueous acetic acid after four hours.

After a second four-hour period, the dialysate is replaced by 0.01 M disodium phosphate. Within about an hour, an opacity is observed within the dialysis bag. The opacity soon changes to a distinct dense white opaque mass, fibrous in form along the longitudinal axis of the dialysis tube. Within four hours, the accumulation of fibrous material at the center of the tube is clearly defined from the remainder of the medium. The dialysate is replaced by fresh 0.02 M disodium phosphate and the apparatus is warmed to 12° to 16°. Solid disodium acid phosphate is added gradually at a rate of about 0.1 meq/hr to the dialysate until the concentration reaches 0.5 M to 1 M. Sufficient sodium chloride is added to the dialysate to provide a concentration of 1 M and dilute aqueous hydrochloric acid added to prevent the pH from exceeding 7.5. Stirring is continued during this time.

Within 12 hours, the collagen fiber has left the center of the dialysis tube and appears as a thick (2 to 3 mm) rope-like structure, twisted upon itself. The medium has become almost clear. The dialysate is replaced by saturated aqueous NaCl and the temperature of the apparatus raised to about ambient temperature (20° to 25°).

After four to six hours at ambient temperature, the dialysate is exchanged for 0.5 percent formaldehyde in a phosphate buffer of about pH 8.0. The dialysis is continued for four hours, at which time the dialysate is replaced by a fresh formaldehyde solution. The dialysis bag now contains moderately constituted dense fibrous micropolymers and some flocculent white material which collects at the bottom of the dialysis bag. The bag is stirred an additional four hours at low speed (approximately 30 rpm) while maintained in the dialysis solution. It is then removed and the small amount of flocculent material separated, followed by reimmersion of the micropolymer fraction in the bag in 1 mM aqueous acetic acid. The solution is cooled to 4° and spun at low speed for an additional four to six hours. After removal of the dialysis bag from the solution, the fibrous micropolymers are collected by centrifugation. They may then be used directly, or stored wet at 4°, or alternatively freeze-dried for indefinite storage.

To prepare a film, the aqueous acetic acid solution containing the fibrous micropolymers may be mixed with collagen in solution to provide a mixture at a desired concentration, usually from about 0.2 to 2% by weight. The solution may be extensively homogenized, preferably in vacuo, employing a degassed suspending medium i.e. aqueous acetic acid. The solution is preferably cooled to 4° and then pumped onto plates in a laminar flow hood at 33° and dried. Further cross-linking can be achieved by exposing the layer to formaldehyde fumes. Successive layers may then be poured over the original layer, with various buffers added to the suspending solution for generating layers of gel-like consistency. The dry sheets are exposed to concentrated ammonia vapor to achieve neutralization, followed by an aqueous acetone (1:1) rinse. The resulting membranes can be sterilized by gas, or exposure to irradiation, heat at 120° C. in vacuo using e.g. gamma-radiation or ultraviolet light. The sterilized membranes are then lyophilized and packaged so as to maintain their aseptic condition.

A burn dressing was prepared as follows. NFMs were dispersed in water, spun down and the process repeated. The collagen was then dispersed in water at a concentration of 20 mg/ml by homogenization. The dispersion was freed of dissolved gases by applying a mild vacuum, followed by pouring the solution into $100 \times 200$ mm pans to provide about 1 g of solids in the tray. The dispersion is then concentrated by slowly evaporating the water in a laminar flow hood under ambient condition. The dispersion is then lyophilized to form a foam, followed by cross-linking the foam by treating it with a 0.1 weight percent formaldehyde solution of 1:1 v/v acetone:water for 20 minutes. The foam is then washed with water.

A collagen film is then laminated to the foam as follows. The film precursor is prepared by dispersing a 1:4 weight ratio of noncross-linked NFM with cross-linked NFM. The cross-linked NFM is obtained by treating NFM with a 0.1 weight percent formaldehyde aqueous solution, 0.2 M in disodium phosphate for 20 minutes. Dispersion was achieved by homogenization to provide a concentration of 10 mg/ml.

After removing dissolved gases by applying a light vacuum, the dispersion is introduced into a tray to provide a layer of about 400 mg solids/200 $cm^2$. The slurry is then frozen at $-20°$ C. The water-washed foam prepared above is applied directly to the solid slurry, entrapped air squeezed out, and then the water is removed by maintaining the laminate at 33° C. until dry. After rehydration with water for one hour, the laminate is lyophilized and then sterilized.

The subject invention provides for nonantigenic atelopeptide collagen in the form of fibrils and fibers which may be used for fabrication of a wide variety of articles or may be used directly as gels for coating various wounds or injuries, e.g. burns, for replacement of vitreous, or the like, for preparation of packings or implants or for the production of membranes, bags, films, sutures, strands, dressings, prosthetic devices or the like for replacement of defective or absent connective tissue e.g. skin, bone, tendon or other mammalian structural members.

The atelopeptide collagen of this invention can also be used for cosmetic purposes, particularly by plastic surgeons for enhancing or forming breasts, in jaws or in other mammalian structural members to modify the size, shape, contour or the like. In accordance with this invention, a collagenous material is achieved which is not rejected when implanted in human or other animals and, depending upon the manner of cross-linking, can have a wide variety of tensile properties approaching or exceeding those of naturally occurring collagen. The manner in which the collagenous fibril is prepared allows for a great degree of flexibility in its subsequent employment, either by itself or in combination with collagen in solution.

The procedures employed in accordance with this invention remove almost all or all of the noncollagen protein and materials other than protein, as well as the immunogenic telopeptides. The resulting atelopeptide collagen is substantially freed of the immunogenic procedures and mechanical and chemical treatment, the atelopeptide collagen is oriented, so as to form fibers which resemble natural collagen fibers. These fibers may then be cross-linked in accordance with known techniques to provide filaments and fibers of varying physical characteristics, as required, resembling or being superior to natural collagen.

The atelopeptide collagen of this invention upon implantation or application to living tissue supports invasion by the host cells. Although the foregoing invention has been described in some detail by way of illustration and example for purposes of clarity of understanding, it will be obvious that certain minor changes and modifications may be introduced within the scope of the appended claims.

We claim:

1. A method of preparing fibers of atelopeptide collagen having physical properties resembling natural collagen fibers which comprises:
   inducing slow desolubilization of atelopeptide collagen from an aqueous solution of atelopeptide collagen while subjecting said solution to a directionally uniform mild shear force of about 30 to about 5000 dynes/$cm^2$ whereby fibers of atelopeptide collagen are formed.

2. A method according to claim 1, wherein said inducing is achieved by having an initial acidic medium to which is slowly added an inorganic alkaline salt.

3. A method according to claim 2, wherein said inorganic alkaline salt is a phosphate.

4. A method according to claim 1, wherein said aqueous solution is contained in a dialysis bag which is slowly rotated in an aqueous inorganic alkaline salt medium.

5. A method according to claim 1, wherein said inducing is achieved by thermal gelation employing a salt solution at about physiological salt concentration and pH.

6. A method according to claim 1, including the step of cross-linking said isolated fibers.

7. A method of preparing fibers of atelopeptide collagen fibrils having physical properties resembling natural collagen fibers which comprises:
slowly adding to a dilute aqueous acidic solution of atelopeptide collagen an inorganic alkaline salt, whereby the ionic strength and pH of the solution are raised, while subjecting said solution to rotational shear forces of about 30 to 5000 dynes/cm$^2$ so that fibers of atelopeptide collagen fibrils come out of solution; and
substantially freeing said fibers of said alkaline salt.

8. A method according to claim 7, including the step of cross-linking said fibers.

9. A method according to claim 8, wherein said cross-linking agent is formaldehyde, glutaraldehyde, chromic sulfate, ultraviolet radiation or heat.

10. A method according to claim 7, wherein said shear force is produced by rotation of said solution at about 20 to 1000 rpm.

11. A method according to claim 10, wherein said aqueous acidic solution is an aqueous acetic acid solution at a concentration in the range of about 0.001 M to 0.1 M and said alkaline salt is disodium acid phosphate which is added to provide a final concentration in the range of about 0.01 M to 0.05 M.

12. The method of claim 1 wherein said fibers have a mean diameter of at least about 500 nm and appear as a rope-like structure in a scanning electron micrograph.

13. The method of claim 7 wherein said fibers have a mean diameter of at least 500 nm and appear as a rope-like structure in a scanning electron micrograph.

14. The method according to claim 1 wherein the shear force is about 75 to 2500 dynes/cm$^2$.

* * * * *